United States Patent [19]

Foguet et al.

[11] Patent Number: 4,883,797
[45] Date of Patent: Nov. 28, 1989

[54] DERIVATIVES OF PIPERAZINE, METHOD FOR MAKING THE SAME

[75] Inventors: Rafael Foguet; Jose A. Ortiz; Santiago Gubert; Manuel M. Raga; Aurelio Sacristan, all of Barcelona, Spain

[73] Assignee: Ferrer Internacional, S.A., Barcelona, Spain

[21] Appl. No.: 143,214

[22] Filed: Jan. 7, 1988

Related U.S. Application Data

[63] Continuation of Ser. No. 786,169, Oct. 9, 1985, abandoned, which is a continuation of Ser. No. 504,846, Jun. 17, 1983, abandoned.

[30] Foreign Application Priority Data

Jun. 17, 1982 [ES] Spain ................................. 514.340

[51] Int. Cl.$^4$ .................... A61K 31/495; C07D 405/06
[52] U.S. Cl. .................................. 514/255; 544/121; 544/357; 544/374; 544/379; 544/388; 544/396; 544/398; 544/402
[58] Field of Search ................ 514/255; 544/374, 379, 544/388, 396, 398, 402

[56] References Cited

PUBLICATIONS

Vigelius et al., "Chemical Abstracts", vol. 81, 1984, col. 63680q.
Zikolova et al., "Chemical Abstracts", vol. 100, 1983, col. 100:6454f.
Kaneko et al., "Chemical Abstracts", vol. 105, 1986, col. 105:105702z.
Kimura et al., "Chemical Abstracts", vol. 106, 1986, col. 106:224372t.
Foguet et al., "Chemical Abstracts", vol. 108, 1983, col. 108:167504c.

Primary Examiner—Glennon H. Hollrah
Assistant Examiner—James H. Turnipseed
Attorney, Agent, or Firm—Michael J. Striker

[57] ABSTRACT

Derivatives of piperazine having the general formula

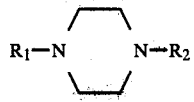

wherein $R_1$ is benzhydryl or cinnamyl and $R_2$ is selected from the group consisting of $-CH_2-CR_3=CHR_4$,

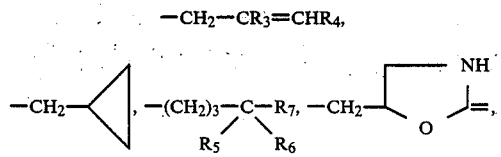

$-(CH_2)_3-R_8$, $-CH_2NHR_9$, $-CH_2NH_2$ and $-COR_{10}$; wherein $R_3$ is hydrogen, chloromethyl, (4-benzhydryl-1-piperazinyl) methyl, 4-morpholinylmethyl or 1-piperidinylmethyl, $R_4$ is hydrogen, chloromethyl or carbethoxy, $R_5$ and $R_6$ taken together are an oxygen atom or the radical $-O-(CH_2)_2-O-$, $R_7$ is methyl, phenyl or 2-thienyl, $R_8$ is 4-morpholinyl, 1-piperidinyl or 4-benzhydryl-1-piperazinyl, $R_9$ is 2-oxo-1-(pyrrolidinyl) acetyl, 2-hydroxybenzoyl or 4-sulfamoylbenzoyl, $R_{10}$ is 2-oxo-1-(pyrrolidinyl)methyl or 4-sulfamoylphenyl and X is oxygen or NH; as well as methods for making the same and their use in a pharmaceutical composition is proposed. The compounds have cardiovascular properties and increasing effects on cerebral flow.

9 Claims, No Drawings

DERIVATIVES OF PIPERAZINE, METHOD FOR MAKING THE SAME

This application is a continuation of application Ser. No. 06/786,169, filed on Oct. 9, 1985, now abandoned, which is a continuation of application Ser. No. 06/504,846, filed on June 17, 1983, now abandoned.

BACKGROUND OF THE INVENTION

The present invention relates to derivatives of piperazine having the general formula (I):

wherein $R_1$ is benzhydryl or cinnamyl, and
$R_2$ is selected from the group consisting of —CH$_2$—CR$_3$=CHR$_4$,

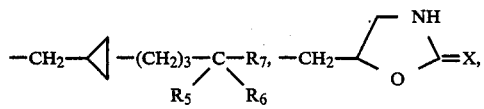

—(CH$_2$)$_3$—R$_8$, —CH$_2$NHR$_9$, —CH$_2$NH$_2$ and —COR$_{10}$, wherein R$_3$ is hydrogen, chloromethyl, (4-benzhydryl-1-piperazinyl) methyl, 4-morpholinylmethyl or 1-piperidinylmethyl, R$_4$ is a hydrogen, chloromethyl or carbethoxy, R$_5$ and R$_6$ together can be an oxygen atom or the sequence —O—(CH$_2$)$_2$—O—, R$_7$ is methyl, phenyl or 2-thienyl, R$_8$ is 4-morpholinyl, 1-piperidinyl or 4-benzhydryl-1-piperazinyl, R$_9$ is 2-oxo-1-(pyrrolidinyl) acetyl, 2-hydroxybenzoyl or 4-sulfamoylbenzoyl, R$_{10}$ is 2-oxo-1-(pyrrolidinyl) methyl or 4-sulfamoylphenyl and X is oxygen or NH, The invention further relates to the non-toxic addition salts of compound I as well as to a method for making the same and to their use in a pharmaceutical composition.

The compounds of the present invention are obtained in accordance with the following methods:

(A) Reacting a monalkyl piperazine of general formula (II):

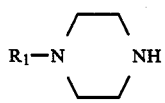

(II)

wherein $R_1$ is as defined for (I), with a reactant selected from an alkyl halide of general formula Y-R$_{11}$ (III) wherein Y is chlorine or bromine and R$_{11}$ is —CH$_2$—CR$_3$=CHR$_4$,

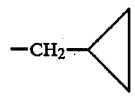

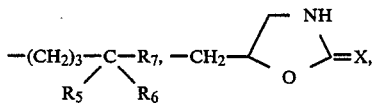

or —(CH$_2$)$_3$—R$_8$, X is oxygen or NH, thus obtaining the compounds of general formula (I) wherein R$_1$ is defined above and R$_2$ is selected from —CH$_2$—CR$_3$=CHR$_4$,

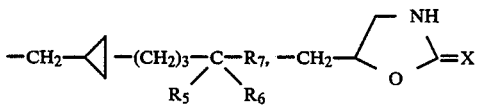

or —(CH$_2$)$_3$—R$_8$, X is Oxygen or NH.

Likewise, the reaction of compounds of general formula (I) wherein R$_1$ is as defined and R$_2$ is —CH$_2$—CR$_3$=CHR$_4$ (R$_3$=chloromethyl, R$_4$=hydrogen) with N-monobenzhydrylpiperazine, morpholine or piperidine yields the compounds of general formula (I) wherein R$_1$ is as defined above and R$_2$ is —CH$_2$—CR$_3$=CHR$_4$ (R$_3$=(4-benzhydryl-1-peperazinyl)-methyl, 4-morpholinylmethyl or 1-piperidinylmethyl; R$_4$=hydrogen).

(B) Reacting the monoalkyl piperazine of general formula (II) with formaldehyde and a reactant selected from an amide of general formula R$_9$NH$_2$(IV) wherein R$_9$ is 2-oxo-1-(pyrrolidinyl) acetyl, 2-hhydroxybenzoyl or 4-sulfamoylbenzoyl, thus obtaining the compounds of general formula (I) wherein R$_1$ is defined above and R$_2$ is —CH$_2$NHR$_9$. These obtained compounds may be hydrolyzed, in an acid medium, to form the corresponding compounds of general formula (I) wherein R$_1$ is as defined above and R$_2$ is —CH$_2$NH$_2$ which, by reaction with a carboxylic acid of general formula R$_9$OH (V) wherein R$_9$ is as defined above, to provide the compounds of general formula (I) wherein R$_1$ is as defined above and R$_2$ is —CH$_2$NHR$_9$.

(C) Reacting the monalkyl piperazine of general formula (II) with a carboxylic acid of general formula R$_{10}$COOH (VI) wherein R$_{10}$ is 2-oxo-1-(pyrrolidinyl)-methyl or 4-sulfamoylphenyl, thus obtaining the compounds of general formula (I) wherein R$_1$ is as defined above and R$_2$ is —COR$_{10}$.

The reaction of the monalkyl piperazine of general formula (II) with the alkyl halides of general formula (III) is suitably conducted in a medium containing an alkanol having 1 to 4 carbon atoms, preferably ethanol, and in the presence of a base selected from either an alkali metal or alkaline earth metal carbonate or bicarbonate, preferably sodium bicarbonate, or a tertiary amine, preferably triethylamine, under reflux. Alkylation of N-monobenzhydrylpiperazine, morpholine or piperidine to yield the compounds of general formula (I) wherein R$_1$ is as defined above and R$_2$ is —CH$_2$—CR$_3$CHR$_4$ (R$_3$=chloromethyl, R$_4$=hydrogen) is carried out in a medium containing an alkanol having 1 to 4 carbon atoms, preferably ethanol, under reflux, thus obtaining respective derivatives of compound I wherein R$_1$ is as defined above and R$_2$ is —CH$_2$—CR$_3$=CHR$_4$ (R$_3$=(4-benzhydryl-1-piperazinyl)-methyl, 4-morpholinylmethyl or 1-piperidinylmethyl; R$_4$=hydrogen).

When the reaction is conducted between the monalkyl piperazine of general formula (II) and an amide of general formula (IV), in the presence of formaldehyde, it is convenient to use an alkanol having 1 to 4 carbon atoms as solvent, preferably ethanol, under reflux. Hydrolysis of the compounds thus obtained, in an acid medium, especially that formed from a mixture of acetic acid and hydrochloric acid, under reflux, leads to the fragmentation of the carboxamide group, thus obtaining the corresponding derivatives of compound I wherein $R_1$ is as defined above and $R_2=-CH_2NH_2$. The reaction of these derivatives with carboxylic acids of general formula (V) is conducted in the presence of carbonyldiimidazole as a catalyst in a medium composed of N,N-dimethylformamide, or an ether, preferably tetrahydrofuran, or mixture of both, and at room temperature, and results in derivatives of compound (I) wherein $R_1$ is as defined above and $R_2$ is $-CH_2NHR_9$ ($R_9=2$-oxo-1-(pyrrolidinyl) acetyl, 2-hydroxybenzoyl or 4-sulfamoylbenzoyl.

In those cases where the reaction occurs between the monalkyl piperazine of general formula (II) and a carboxylic acid of general formula (VI), carbonylidiimidazole is also used as a catalyst and N,N dimethylformamide or an ether, preferably tetrahydrofuran, or a mixture thereof is used as a solvent.

Compounds of the present invention have cardiovascular properties and it should be emphasized a remarkable, i.e., marked, increasing effect on cerebral blood flow as experimentally determined by an electromagnetic flowmeter. Results of experimental cardiovascular assessment are shown hereinafter for the known substances Aligeron and Cinnarizine and for the active compounds (Tables 1 (i) and 1 (ii).

TABLE 1(i)

| Parameters Compounds | Antiarrythmic activity $ED_{50}$ (mg/Kg) -1- | Mean arterial pressure, Hypotension $ED_{50}$ (mg/kg) -2- | Heart rate, Bradycardia $ED_{50}$ (mg/kg) -3- |
|---|---|---|---|
| 1 | 4.2 | 2.7 | 3.4 |
| 6 | 4.3 | 1.5 | 1.7 |
| 7 | 23.0 | 2.1 | 3.8 |
| 11 | 6.9 | 0.43 | 2.1 |
| 13 | 4.0 | 1.5 | 2.6 |
| 15 | 16.5 | 1.2 | 3.0 |
| Cinnarizine 2HCl | 23.0 | 1.0 | 2.8 |
| Aligeron-2HCl | 4.4 | 1.3 | 4.8 |

| Parameters Compounds | Cerebral flow Increase (%) -4- | Carotid flow Decrease (%) -5- | Arterial pressure Decrease (%) -6- | Cerebral vascular resistance Decrease (%) -7- |
|---|---|---|---|---|
| 1 | 55.0 | 68.0 | 30.0 | 55.0 |
| 6 | 70.0 | 22.0 | 58.0 | 75.3 |
| 7 | 32.0 | 13.0 | 27.3 | 44.7 |
| 11 | 81.0 | 40.9 | 50.0 | 74.0 |
| 13 | 140.1 | 25.7 | 35.0 | 73.1 |
| 15 | 38.5 | 60.0 | 45.5 | 60.3 |
| Cinnarizine 2HCl | 76.7 | 62.8 | 43.0 | 68.0 |
| Aligeron 2HCl | 64.0 | 21.3 | 36.0 | 61.0 |

Antiarrhythmic activity (Parameter 1) has been determined according to the method of Ferrini et al (Arzn.-Forsch., 29 (II), 9a, 1947-77, 1979). Compounds were endovenously administered to mice and results have been tabulated as $ED_{50}$ values.

The decrease in arterial pressure (Parameter 2) and the effects on heart rate (Parameter 3) have been evaluated according to the usual conventional methods used in Cardiovascular Pharmacology. Compounds were endovenously administered to anesthetized rats and results have been tabulated as $ED_{50}$ values.

The measurements of cerebral and carotid flow changes (parameters 4 and 5) have been made using the most sophisticated methods. Both parameters have been measured by electromagnetic flowmetry (Narcomatic-Electromagnetic flowmeter) on 12 anesthetized dogs. The hemodynamic parameter average of animals before testing were $pO_2=95.40\pm3.98$; $pCO_2=34.31\approx2.38$ and pH-7.297$\pm$0.315 by endovenously administering the compounds of a 5 mg/kg dosis.

Simultaneously with the measuring of cerebral and carotid flows, the mean arterial pressure and cerebral vascular resistance (parameters 6,7) in each animal was determined. These parameters were measured according to the conventional method in Cardiovascular Pharmacology and the values were tabulated as the variation rate (Increase or Decrease) over mean values before testing.

The toxicity of some compounds was determined and found to be lower than Aligeron and Cinnarizine which makes these compounds very useful in therapy. The $LD_{50}$ was endovenously determined in mice according to the Reed-Muench's method as modified by Pizzi (Human Biology, 22(3), 151-190, 1950) and results are set out hereafter in comparison with Aligeron and Cinnarizine (Table 2).

TABLE 2

| Compounds | Acute toxicity $LD_{50}$ (mg/kg) |
|---|---|
| 1 | 25.6 ± 4.39 |
| 6 | 8.6 ± 0.54 |
| 7 | 100.0 ± 6.27 |
| 11 | 21.0 ± 1.72 |
| 13 | 42.5 ± 3.05 |
| 15 | 40.0 ± 4.19 |
| Cinnarizine 2HCl | 47.6 ± 5.25 |
| Aligeron 2HCl | 38.5 ± 1.06 |

Compounds of the present invention mixed with pharmaceutically acceptable carriers can be administered by the oral route in the form of tablets, capsules, syrup, solution, etc., by injectible route and by rectal route, at daily doses ranging from 50 to 500 mg.

EXAMPLES

The following examples will further illustrate the preparation of compound I of the invention:

EXAMPLE 1

1-Benzhydryl-4-cyclopropylmethyl-piperazine dihydrochloride (Compound 1)

(I, $R_1$=benzhydryl, $R_2$=cyclopropylmethyl)

14.0 g of N-morobenzhydryl-piperazine (0.055 mole) are dissolved in 100 ml of absolute ethanol in the presence of 6.5 g of sodium bicarbonate (0.077 mole). The resulting mixture is gently treated with 6.03 g solution of chloromethylcyclopropane (0.066 mole) in 10 ml of absolute ethanol, then it is subjected to reflux for 20 hours. After conditioning the reaction mass to room temperature, the reaction product is then filtered off and the ethanol is removed by distillation. The resulting crude product is dissolved in 100 ml of 3N hydrochloric acid, washed with ethyl ether and extracted with chloroform. The organic extracts are dried over anhydrous magnesium sulphate, filtered off and the solvent is removed by distillation. The resulting crude product is recrystallized from 96% ethanol, thus obtaining 11.5 g of crystals of 1-benzhydryl-4-cyclopropylmethylpiperazine dihydrochloride. Yield: 55%; m.p.: 245°–247° C.

(d); IR(KBr), cm$^{-1}$: 3000–2900, 2800–2400, 770, 755, 715, 705.

EXAMPLE 2

According to the process described in Example 1 and using corresponding starting intermediates, the compounds listed in Table 3 are obtained.

TABLE 3

| Compounds | $R_1$ | Compound(I) $R_2$ | Base or Salt | M.p. °C. |
|---|---|---|---|---|
| 2 | $(C_6H_5)_2CH-$ | $-CH_2-CH=CH-CH_2-Cl$ | Base | 174–176 |
|   |   |   | 2HCl | 215–221 |
| 3 | $(C_6H_5)_2CH-$ | $-CH_2-C(=CH_2)(CH_2Cl)$ | Base | 77,5–77,9 |
| 4 | $(C_6H_5)_2CH-$ | $-CH_2-C(=CH_2)-CH_2N\text{-piperazine-}N-CH(C_6H_5)_2$ | Base | 139–142 |
| 5 | $(C_6H_5)_2CH-$ | $-CH_2-C(=CH_2)-CH_2N\text{-morpholine}$ | Base | 167–171 |
| 6 | $(C_6H_5)_2CH-$ | $-CH_2-C(=CH_2)-CH_2N\text{-piperidine}$ | Base | 99–102 |
| 7 | $(C_6H_5)_2CH-$ | $-CH_2-CH=CH-COO_2H_5$ | 2HCl | 217,5–218 |
| 8 | $C_6H_5-CH=CH-CH_2-$ | $-CH_2\text{-cyclopropyl}$ | 2HCl | >250 (d) |
| 9 | $(C_6H_5)_2CH-$ | $-(CH_2)_3Co\text{-thienyl(S)}$ | Base | 105–108 |
| 10 | $(C_6H_5)_2CH-$ | $-(CH_2)_3-C(CH_3)(OCH_2CH_2O)\text{-dioxolane}$ | Base | 73–75 |
| 11 | $(C_6H_5)_2CH-$ | $-(CH_2)_3CO-C_6H_5$ | 2HCl | 209–212 |
| 12 | $(C_6H_5)_2CH-$ | $-(CH_2)_3COCH_3$ | 2HCl | 211–212 |
| 13 | $(C_6H_5)_2CH-$ | $-(CH_2)_3-C(C_6H_5)(OCH_2CH_2O)\text{-dioxolane}$ | Base | 93–97 |
| 14 | $(C_6H_5)_2CH$ | $-CH_2\text{-}\begin{pmatrix}NH\\O\end{pmatrix}=O$ | 2HCl | 122–130 |

TABLE 3-continued

| Compounds | R$_1$ | Compound(I) R$_2$ | Base or Salt | M.p. °C |
|---|---|---|---|---|
| 15 | (C$_6$H$_5$)$_2$CH | —CH$_2$—[NH/O ring]=O | 2HCl | 180–190 |
| 16 | C$_6$H$_5$—CH=CH—CH$_2$— | —(CH$_2$)$_3$—N(morpholine) | 3HCl | >250 (d) |
| 17 | C$_6$H$_5$—CH=CH—CH$_2$— | —(CH$_2$)$_3$—N(piperidine) | 3HCl | >250 (d) |
| 18 | (C$_6$H$_5$)$_2$CH— | —(CH$_2$)$_3$—N(piperazinyl)N—CH(C$_6$H$_5$)$_2$ | 4HCl | 240-2 (d) |

EXAMPLE 3

(a) 1-Benzhydryl-4-(2-(1-piperidinylmethyl)-2-propenyl)piperazine (Compound 6)

(I, R$_1$=benzhydryl, R$_2$=2-(1-piperidinylmethyl)-2-propenyl) from 1-benzhydryl-4-(2-chloromethyl-2-propenyl)-piperazine (Compound 3)

(I, R$_1$=benzhydryl, R$_2$=2-chloromethyl-2-propenyl)

A mixture of 7.0 g of 1-benzhydryl-4-(2-chloromethyl-2-propenyl)-piperazine (0.0205 mole) and 6.98 g of piperidine (0.082 mole) in 150 ml of absolute ethanol is heated until it has dissolved completely, and subjected to reflux for 3 hours. Then, it is conditioned to room temperature and the ethanol is removed by distillation. The resulting crude reaction product is treated with distilled water several times until a solid material is obtained which is then filtered and washed abundantly with water. By recrystallization from ethanol, 7.4 g crystals of 1-benzhydryl-4-(2-(1-piperidinylmethyl)-2-propenyl)-piperazine (I, R$_1$=benzhydryl, R$_2$=2-(1-piperidinylmethyl-2-propenyl) are obtained. Yield: 94%; m.p. 99°–102° C.

(b) 1-Benzhydryl-4(2-(4-benzhydryl-1-piperazinyl)methyl)-2-propenyl)-piperazine (Compound 4)

(I, R$_1$=benzhydryl, R$_2$=2-(4-benzhydryl-1-piperazinyl)methyl)-2-propenyl) from 1-benzhydryl-4-(2-chloromethyl-2-propenyl)piperazine (Compound 3)

(I, R$_1$=benzhydryl, R$_2$=2-chloromethyl-2-propenyl)

As described above (a) and using N-monobenzhydryl-piperazine in place of piperidine, Compound 4 is obtained; m.p. 139°–142° C.

(c) 1-Benzhydryl-4-(2-(4-morpholinymethyl)-2-propenyl)piperazine (Compound 5)

(I, R$_1$=benzhydryl, R$_2$=2-(4-morpholinylmethyl)-2-propenyl) from 1-benzhydryl-4-(2-chloromethyl-2-propenylpiperazine) (Compound 3)

(I, R$_1$=benzhydryl, R$_2$=2-chloromethyl-2-propenyl)

As described above (a) and using morpholine in place of piperidine, Compound 5 is obtained; m.p. 167°–171° C.

EXAMPLE 4

1-Benzhydryl-4-(2-oxo-1-(pyrrolidinyl)methylpiperazine (Compound 19)

(I, R$_1$=benzhydryl, R$_2$=(2-oxo-1-(pyrrolidinyl)acetyl)methyl)

5.04 g of N-monobenzhydryl-piperazine (0.02 mole) and 2.84 g of 2-oxo-1-pyrrolidinylacetamide (0.02 mole) are dissolved in 100 ml of absolute ethanol, then 2.6 ml of 35% (p.v) formaldehydr solution is added and the reaction mixture subjected to reflux for 12 hours. The reaction mixture is allowed to stand under stirring for 20 hours at room temperature. The ethanol is removed by distillation and the resulting oil is treated with 60 ml of ethyl ether for 1 hour, thus yielding a crystal-like solid which is filtered, washed with ethyl ether and dried under vaccum. 6.9 g crystals of 1-benzhydryl-4-(2-oxo-1(pyrrolidinyl)acetyl)methyl-piperazine (I, R$_1$=benzhydryl, R$_2$=(2-oxo-1-(pyrrolidinyl)acetyl)methyl) are obtained. Yield: 85%; m.p. 157 158, 5° C.; IR (KBR), cm$^{-1}$: 3460, 3220, 1705, 1680, 1545.

EXAMPLE 5

As described in Example 4 and using the corresponding starting intermediates, the Compounds listed below (Table 4) are obtained.

TABLE 4

| Compounds | R₁ | Compound (I) R₂ | Salt | M.p. °C. |
|---|---|---|---|---|
| 20 | (C₆H₅)₂CH— | 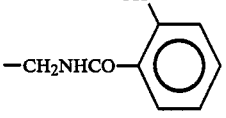 | 2HCl | 158–162 |
| 21 | (C₆H₅)₂CH— | 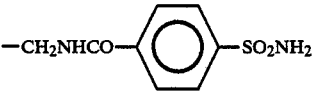 | HCl | 265–6 (d) |

EXAMPLE 6

1-Benzhydryl-4-aminomethyl-piperazine trihydrochloride (Compound 22)

(I, R₁=benzhydryl, R₂=aminomethyl)

3.80 g of 1-benzhydryl-4-(2 oxo-1-(pyrrolidinyl)acetyl)methylpiperazine (0.0093 mole) are treated with 20 ml of glacial acetic acid and 40 ml of 3N hydrochloric acid, and subjected to reflux for 2 hours. Once the reaction is completed, the solvents are removed by distillation under vacuum. The resulting crude reaction product is treated with 100 ml of acetone thus yielding a crystalline solid which is dried under vacuum. 2.05 g crystals of 1-benzhydryl-4-aminomethyl-piperazine trihydrochloride (I, R₁=benzhydryl, R₂=aminomethyl). Yield: 56%; m.p. >250° C. (d). IR (KBr), cm⁻¹: 1590, 1400, 750, 710.

EXAMPLE 7

1-Benzhydryl-4-(4-sulfamoylbenzoyl)amino)methyl-piperazine hydrochloride (Compound 21)

(I, R₁=benzhydryl, R₂=(4-sulfamoylbenzoyl)amino)methyl)

2.01 g of 4-sulfamoylbenzoic acid (0.01 mole) and 1.62 g of carbonyldiimidazol (0.01 mole) are dissolved in 40 ml of N,N-dimethyl-formamide. The mixture is allowed to stand under stirring for 4 hours at room temperature and then 2.81 g of 1-benzhydryl-4-aminomethyl-piperazine (0.01 mole) in 40 ml of dry tetrahydrofurane are added. The resulting mixture is allowed to stand under stirring for 3 hours at room temperature. The reaction liquid is treated with 100 ml of ethyl acetate and 100 ml of distilled water. The two phases are separated and the organic phase is washed with water. The ethyl acetate is removed by distillation and the resulting solid reaction product is treated with 100 ml of ethyl ether, filtered and washed with ether, then dissolved in ethanol and finally 20 ml of saturated hydrogen chloride are added, thus obtaining 2.35 g crystals of 1-benzhydryl-4-(4-sulfamoylbenzoyl)amino)-methyl-piperazine (I, R₁=benzhydryl-4-(sulfamoylbenzoyl)amino)methyl). Yield: 47%; m.p. 265°–266° C. (d). IR (KBr), cm⁻¹: 3240, 1630, 1345, 1160.

EXAMPLE 8

1-Benzhydryl-4-(4-sulfamoylbenzoyl)piperazine (Compound 23) (I, R₁=benzhydryl, R₂=4-sulfamoylbenzoyl)

20.01 g of 4-sulfamoylbenzoic acid (0.01 mole) and 1.62 g of carbonylidiimidozol (0.01 mole) are dissolved in 40 ml of anhyrous N,N-dimethylformamide. The mixture is allowed to stand under stirring for 3 hours at room temperature and then 2.52 g of N-monobenzhydryl-piperazine (0.01 mole) are added. The solution thus obtained is allowed to stand under stirring for 24 hours at room temperature. Then, 100 ml of distilled water and 100 ml of ethyl acetate are added; the two phases are separated and the organic phase is washed with distilled water, then dried over anhydrous magnesium sulphate, filtered and the ethyl acetate is removed by distillation under vacuum. The resulting crude reaction product is treated with ethyl ether and 2.9 g crystals of 1-benzhydryl-4-(4-sulfamoylbenzoyl)piperazine (I, R₁=benzhydryl, R₂=4-sulfamoylbenzoyl) are obtained. Yield: 67%; 228°–231° C. IR (KBr), cm⁻¹: 3260, 3400, 1630, 1170, 1345.

EXAMPLE 9

1-Benzhydryl-4-(2-oxo-1-(pyrrolidinyl)acetyl)piperazine (Compound 24)

(I, R₁=benzhydryl, R₂=2-oxo-1-(pyrrolidinyl)acetyl)

As described in Example 8 and using 2-oxo-1-(pyrrolidinyl) acetic acid in place of 4-sulfamoylbenzoic acid, Compound 24 is obtained, m.p. 169°–170° C. Dihydrochloride, m.p. 204°–206° C.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A compound having the formula

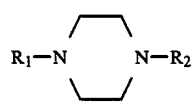

wherein R₁ is benzhydryl or cinnamyl, and R₂ is selected from the group consisting of —CH₂—CR₃=CHR₄,

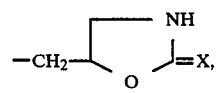

-continued

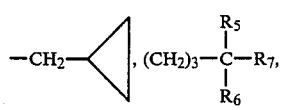

—CH$_2$NHR$_9$, —CH$_2$NH$_2$, and —COR$_{10}$, wherein R$_3$ is hydrogen or chloromethyl, R$_4$ is hydrogen, chloromethyl or carbethoxy, R$_5$ and R$_6$ taken together are oxygen or the sequence

—O—(CH$_2$)$_2$—O—,

R$_7$ is methyl, phenyl or 2-thienyl,

R$_9$ is 4-sulfamoylbenzoyl

R$_{10}$ is 4-sulfamoylphenyl and

X is oxygen or NH.

2. The non-toxic addition salts of the compound of claim 1.

3. A compound according to claim 1 having the formula

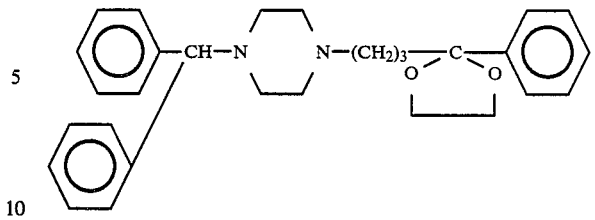

4. A pharmaceutical composition comprising a compound according to claim 1 as active ingredient in admixture with a pharmaceutically acceptable carrier.

5. A pharmaceutical composition as defined in claim 4 in dosage unit form.

6. A pharmaceutical composition as defined in claim 5 containing 50–500 mg of active ingredient per dosage unit.

7. A pharmaceutical composition according to claim 4 comprising

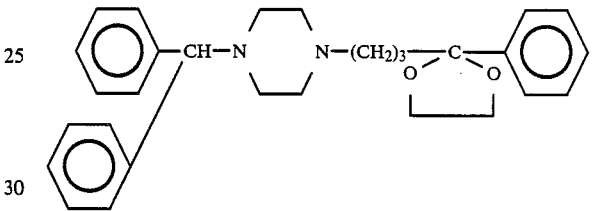

as active ingredient.

8. Method of increasing cerebral flow which comprises administering to a mammal a therapeutically effective amount of the composition of claim 7.

9. Method of improving cardiovascular status quo of a mammal which comprises administering a therapeutically effective amount of a composition according to claim 7.

* * * * *